United States Patent

Peet et al.

[11] Patent Number: 5,965,548
[45] Date of Patent: Oct. 12, 1999

[54] $\Delta^{16}$ UNSATURATED $C_{17}$ HETEROCYCLIC STEROIDS USEFUL AS STEROID $C_{17-20}$ LYASE INHIBITORS

[75] Inventors: Norton P. Peet, Cincinnati, Ohio; Joseph P. Burkhart, Plainfield, Ind.; Cynthia A. Gates, Fairfield, Ohio

[73] Assignee: Merrel Pharmaceuticals, Inc., Bridgewater, N.J.

[21] Appl. No.: 09/072,778

[22] Filed: May 6, 1998

Related U.S. Application Data

[62] Division of application No. 08/795,577, Feb. 6, 1997, abandoned, which is a division of application No. 08/624,395, filed as application No. PCT/US94/11030, Sep. 29, 1994, Pat. No. 5,677,293, which is a continuation of application No. 08/143,679, Oct. 27, 1993, abandoned.

[51] Int. Cl.⁶ .................................................. A61K 31/58
[52] U.S. Cl. ............................................ 514/172; 514/880
[58] Field of Search ............................................... 514/172

[56] References Cited

U.S. PATENT DOCUMENTS

| | | |
|---|---|---|
| 3,431,258 | 3/1969 | Lefebvre et al. . |
| 3,436,390 | 4/1969 | Lefebvre et al. . |
| 4,259,240 | 3/1981 | Wiesner et al. . |
| 5,232,917 | 8/1993 | Bolger et al. . |

FOREIGN PATENT DOCUMENTS

| | | |
|---|---|---|
| 0071460 | 2/1983 | European Pat. Off. . |
| 1081647 | 8/1967 | United Kingdom . |

OTHER PUBLICATIONS

Biggerstaff, et al., J. of Med. Chem. 12(1):1–5 (1969).
Doorenbos, et al., J. Org. Chem. 31(10):3193–3199 (1969).
Barton, et al., Tetrahedron 46(21):7587–7598 (1990).
Wiesner, et al., Helvetica Chimica Acta 65(7):2049–60 (1982).
P. Drasar, et al., Collection of Czechoslovak Chemical Comm.54(12), 3339–3347 (1989).
G. Rapi, et al., European J. of Med. Chem. Chemica Therapeutics 20(3) 277–282 (1985).
P. Drasar et al., J. of Chromatography 283, 396–400 (1984).

*Primary Examiner*—Rebecca Cook
*Attorney, Agent, or Firm*—Mark C. Nelligan

[57] ABSTRACT

The present invention relates to $\Delta^{16}$ unsaturated steroids which are useful as steroid $C_{17-20}$ lyase inhibitors.

12 Claims, No Drawings

$\Delta^{16}$ UNSATURATED $C_{17}$ HETEROCYCLIC STEROIDS USEFUL AS STEROID $C_{17-20}$ LYASE INHIBITORS This application is a divisional application of Ser. No. 08/795,577, filed Feb. 6, 1997, now abandoned, which is a division of prior application Ser. No. 08/624,395, filed Jul. 15, 1996, now U.S. Pat. No. 5,677,293, which is the U.S. National Stage filing under 35 USC 371 of PCT/US94/11030, filed Sep. 29, 1994 which is a continuation of U.S. Ser. No. 08/143,679, filed Oct. 27, 1993, now abandoned, which are hereby incorporated by reference.

BACKGROUND OF THE INVENTION

It is estimated that 75% of prostatic cancers are sensitive to levels of androgens, more specifically testosterone. (Van Wauwe, J. P. and Janssen, P. A. J., *J. Med. Chem.*, (1989), 32, 2233). It is well established that reduction of serum testosterone levels is useful in the treatment of such prostatic cancers. In clinical practice, this has been accomplished for example by orchiectomy or by diethylstilbestrol treatment. However, the first approach is often psychologically unacceptable while a number of side effects are associated with the second approach.

The cytochrome P-450$_{17\alpha}$ monooxygenase enzyme system catalyzes the 17α-hydroxylation of $C_{21}$ steroids and also catalyzes the oxidative cleavage of the $C_{17-20}$ bond. (Blohm, T. R. et al., *Biochem. Biophys. Res. Commun.*, (1989), 162, 1571). More specifically the steroid $C_{17-20}$ lyase activity of cytochrome P-450$_{17\alpha}$ catalyzes the conversion of the $C_{21}$ steroids pregnenolone and progesterone to the $C_{19}$ steroids dehydroepiandrosterone and androstenedione, which are the precursors of the androgens, 5α-dihydrotestosterone and testosterone. Androstenedione and testosterone, in turn, are the Precursors of the estrogens, estrone and estradiol. Thus, inhibition of the steroid $C_{17-20}$ a lyase can reduce formation of the androgens as well as the estrogens. As a result of this effect, the search for effective and selective inhibitors of the steroid $C_{17-20}$ lyase enzyme is expanding. (Laughton, C. A. and Neidle, S., *Biochem. Biophys. Res. Commun.*, (1990), 171, 1160). $C_{17-20}$ lyase inhibitors would be useful for treating various androgen-dependent disorders. More particularly, such compounds would be useful in the treatment of prostatic-carcinoma, benign prostatic hyperplasia, male-pattern baldness and virilism and hirsutism (in women). In addition, $C_{17-20}$ lyase inhibitors would also be useful in the treatment of estrogen-dependent disorders, such as estrogen dependent breast cancer.

Thus, in light of the drawbacks associated with diethylstilbestrol treatment or orchiectomy, there has been an ongoing search for effective inhibitors of steroid $C_{17-20}$ lyase. The present invention relates to $C_{17}$ heterocyclic steroids and also to a method for using such compounds as effective steroid $C_{17-20}$ lyase inhibitors. More particularly, the present invention relates to the treatment of androgen dependent disorders.

SUMMARY OF THE INVENTION

The present invention relates to compounds having the following general formula I:

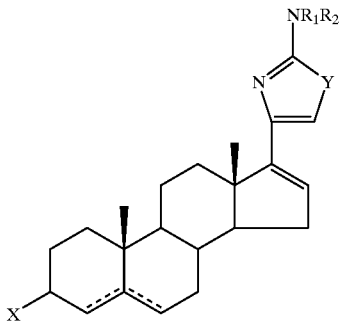

formula I wherein
= represents a single or double bond;
X is =O or —OH; and
Y is S, O, or NR;
wherein
R, $R_1$ and $R_2$ are each independently hydrogen or $C_1$–$C_4$ alkyl;
or a pharmaceutically acceptable salt and/or solvate thereof.

The present invention further provides a method of inhibiting the steroid $C_{17-20}$ lyase activity in a patient in need thereof comprising administering to said patient an effective inhibitory amount of a compound of formula II:

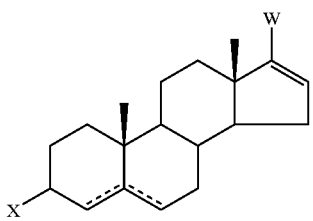

formula II wherein
= represents a single or double bond;
X is =O or —OH;
W is selected from the group consisting of;

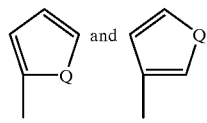

wherein
Q is O, S or NR;
wherein
R is hydrogen or $C_1$–$C_4$ alkyl;
or a pharmaceutically acceptable salt thereof.

The present invention further provides a method of inhibiting the steroid $C_{17-20}$ lyase activity in a patient in need thereof comprising administering to said-patient an effective inhibitory amount of a compound of formula (I).

The present invention further provides a method of treating a patient suffering from an androgen dependent disorder comprising administering to said patient an effective inhibitory amount of a compound of formulas (I) or (II).

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl, and the like. The term "halogen" or "halo" refers to a chlorine, bromine or iodine atom.

The term "stereoisomer" refers to a compound made up of the same atoms bonded by the same bonds but having different three-dimensional structures which are not interchangeable. The three dimensional structures are called configurations.

It is understood that these compounds of formulas (I) and (II) may exist in a variety of stereoisomeric configurations. These stereoisomers are specifically understood to be included within the scope of the present invention.

The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicylic, hydroxyethanesulfonic, ethylenesulfonic, halobenzenesulfonic, toluenesulfonic, naphthalenesulfonic, sulfanilic and the like. Such salts can exist in either a hydrated, solvated or substantially anhydrous form. The hydrobromide is preferred as the pharmaceutically acceptable salt of compounds of formula I.

The term "solvate" refers to a compound of formula (I) or the pharmaceutically acceptable salt of formula (I) wherein molecules of a suitable solvent are incorporated in the crystal lattice. A suitable solvent is not substantially toxic at the dosage administered as the solvate to achieve the desired effect. Examples of suitable solvents are ethanol and the like.

The general steroid skeletal structure and corresponding numbering system is described by structure A;

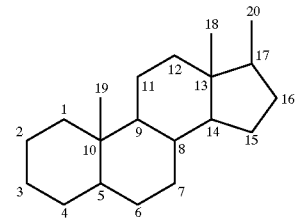

A

The compounds of formula I as defined by formulas Ia and Ib can be prepared as described in Schemes I and II. All substituents, unless otherwise indicated, are previously defined. The reagents and starting materials are readily available to one of ordinary skill in the art.

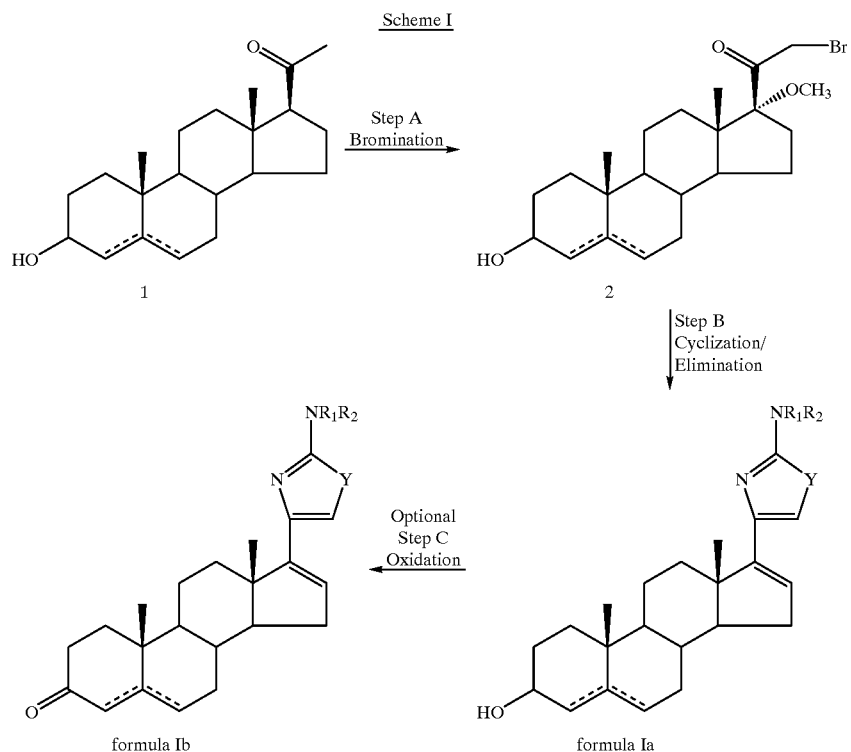

In Scheme I step A, the steroid described by structure (1) undergoes a bromination reaction to provide the brominated steroid described by structure (2).

For example, an appropriately substituted steroid (1), such as pregnenolone is dissolved in a suitable organic solvent, such as methanol and treated with an excess of copper (II) bromide. The mixture is heated at reflux from about 2 to 24 hours. After cooling, the reaction is filtered and the product isolated and purified by techniques well known in the art, such as extractive methods and recrystallization. For example, the filtrate is reduced under vacuum, the residue dissolved in a suitable organic solvent, such as methylene chloride and the organic rinsed with water, half saturated aqueous sodium bicarbonate and brine. The organic is then dried over a suitable drying agent, such as anhydrous sodium sulfate, filtered and concentrated under vacuum. The residue is then recrystallized from a suitable organic solvent, such as acetone to provide brominated steroid (2).

In Scheme I, step B the brominated steroid (2) is subjected to a cyclization/elimination reaction by treatment with suitable urea, thiourea or guanidine to provide the $C_{17}$ heterocyclic steroid described by formula Ia wherein X of formula I is OH. Examples of suitable ureas, thioureas or guanidine are urea, thiourea, guanidine, 1-methyl-2-thiourea, benzylurea, 1-ethylguanidine and the like.

For example, the brominated steroid (2) is suspended in a suitable organic solvent, such as ethanol. The suspension is treated with an excess of a suitable urea, thiourea or guanidine and heated to reflux for approximately 1.5 hours. About half of the solvent is distilled off during reflux. The reaction is cooled to room temperature, filtered and the solid washed with a suitable organic solvent, such as ethanol. The obtained solid is dried under high vacuum to provide the $C_{17}$ heterocyclic steroid of formula Ia.

In Scheme I, step C the $C_{17}$ heterocyclic steroid of formula Ia is oxidized to the ketone derivative of the $C_{17}$ heterocyclic steroid described by formula Ib.

For example, oxalyl chloride is dissolved in a suitable organic solvent, such as methylene chloride under an inert atmosphere, such as nitrogen. The solution is cooled to approximately −55° C. and approximately 1.2 equivalents of dimethylsulfoxide are added dropwise to the stirring solution. After stirring for about 3 minutes, about 0.33 equivalents of the $C_{17}$ heterocyclic steroid of formula Ia dissolved in a suitable organic solvent mixture, such as methylene chloride/dimethylsulfoxide (2:1), is slowly added to the reaction dropwise. After addition is complete the reaction is stirred at −55° C. for about 30 minutes. An excess of a suitable base, such as triethylamine, is added and after approximately 5 minutes the reaction is allowed to warm to room temperature. The product is then isolated and purified by techniques well known in the art, such as extractive methods and flash chromatography. For example, the reaction is diluted with methylene chloride, rinsed with dilute sodium bicarbonate, brine, dried over anhydrous magnesium sulfate, filtered and concentrated under vacuum. The residue is then purified by flash chromatography using a suitable eluent mixture of organic solvents, such as ethyl acetate/hexane on a stationary phase of silica gel. The purified product can then be recrystallized from a suitable solvent mixture, such as ethyl acetate/hexane to provide the $C_{17}$ heterocyclic steroid described by formula Ib.

Alternatively in Scheme II compounds of formula Ia and Ib can be prepared from the starting material described by structure (3).

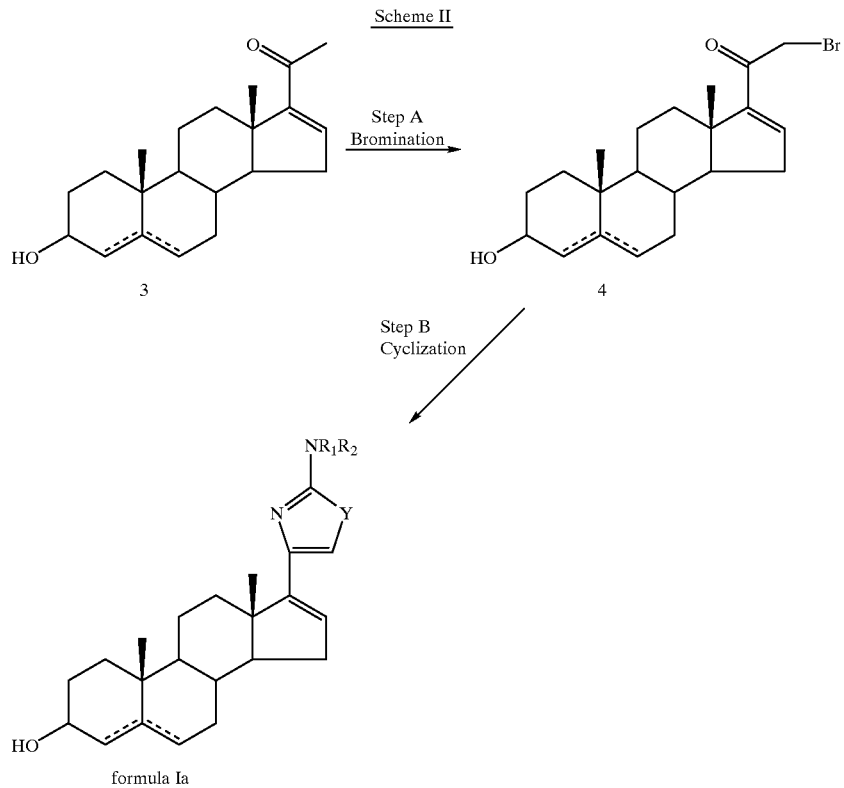

For example in Scheme II, step A, an appropriately substituted steroid (3), such as 16-dehydropregnenolone is dissolved in a suitable organic solvent, such as tetrahydrofuran and treated with an excess of 5,5-dibromobarbituric acid. Concentrated aqueous hydrogen bromide is added and the reaction is heated at reflux for approximately one hour. After cooling, the reaction is concentrated under vacuum. The product is isolated and purified by extractive techniques and recrystallization as described previously in Scheme I, step A to provide the brominated steroid described by structure (4).

In Scheme II, step B the brominated steroid (4) is subjected to a cyclization reaction by treatment with a suitable urea or thiourea to provide the $C_{17}$ heterocyclic steroid described by formula Ia wherein X of formula I is OH.

For example, the brominated steroid (4) is suspended in a suitable organic solvent, such as ethanol. An excess of a suitable urea or thiourea is added and the reaction is heated to reflux for approximately one hour. Approximately half of the solvent is distilled off during reflux. The reaction is cooled to room temperature and the reaction is filtered. The solid is rinsed with ethanol, dried under high vacuum and recrystallized from a suitable solvent, such as ethanol to provide the $C_{17}$ heterocyclic steroid described by formula Ia.

The $C_{17}$ heterocyclic steroid described by formula Ia is then oxidized to the $C_{17}$ heterocyclic steroid described by formula Ib as described previously in Scheme I, step C.

The compounds of formula II can be prepared as described in Scheme III. All substituents, unless otherwise indicated, are previously defined. The reagents and starting materials are readily available to one of ordinary skill in the art.

W. Greene "Protective Groups in Organic Synthesis", John Wiley and Sons, Inc., 1981, chapter 2.

For example, the steroid (5), such as dehydroisoandrosterone is dissolved in a suitable organic solvent, such as dimethylformamide under an inert atmosphere, such as nitrogen. An equivalent of a suitable protecting group reagent, such as t-butyldimethylsilyl chloride is added to the solution. A slight excess of a suitable organic base is added, such as triethylamine along with a catalytic amount of 4-dimethylamnopyridine. The reaction is stirred at room temperature for one to two days. The product is isolated and purified by techniques well known in the art, such as extractive methods and flash chromatography. For example the reaction is diluted with water and the solid collected by filtration. The solid is then dissolved in a suitable organic solvent, such as ethyl acetate, rinsed with dilute hydrochloric acid, half saturated sodium bicarbonate, brine, dried over anhydrous magnesium sulfate, filtered and concentrated under vacuum. The residue is then purified by flash chromatography using a suitable eluent, such as ethyl acetate/

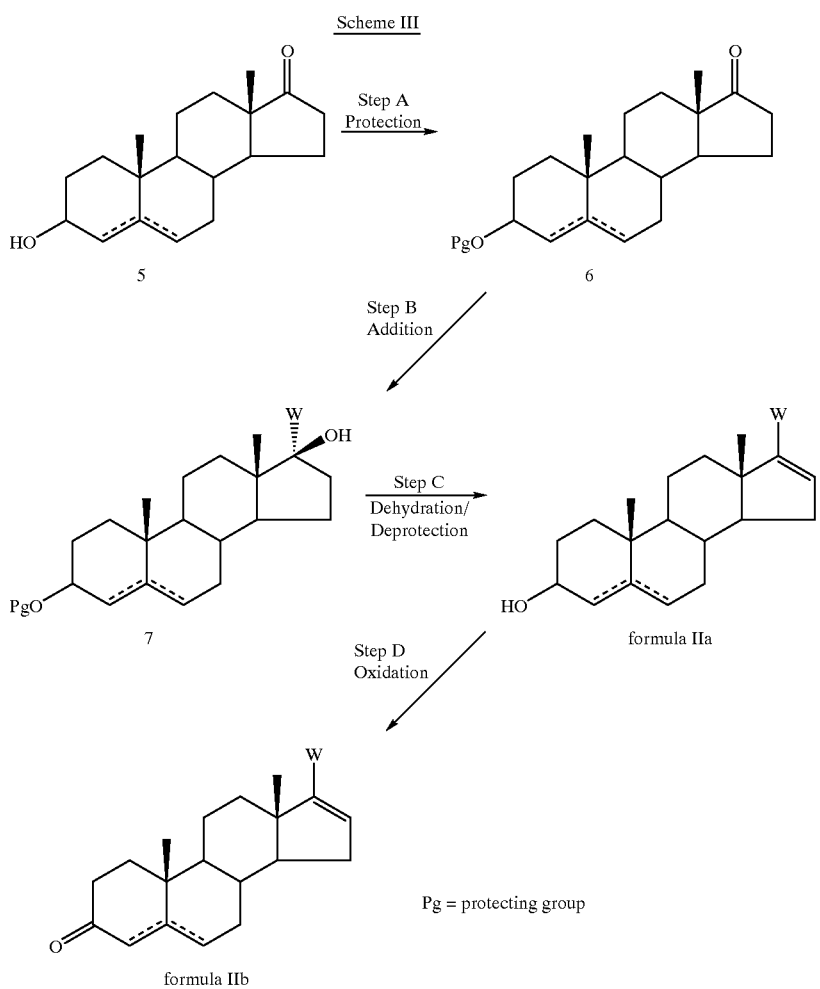

In Scheme III, step A the 3-hydroxy substituent on the steroid described by structure (5) is protected with a suitable protecting group to provide the protected steroid described by structure (6). Examples of suitable protecting groups for a hydroxy substituent along with the methods of preparing and methods of cleavaging such groups are described by T.

hexane on a suitable stationary phase, such as silica gel to provide the protected steroid (6).

In Scheme III, step B the protected steroid (6) is subjected to an addition of a heterocycle described by W to provide the $C_{17}$ heterocyclic steroid described by structure (7).

For example, an excess of appropriately substituted heterocycle is dissolved in a suitable anhydrous organic solvent, such as tetrahydrofuran under an inert atmosphere, such as nitrogen. Examples of appropriately substituted heterocycles are thiophene, furan, 3-bromothiophene, 3-bromofuran and the like. A suitable alkyllithium, such as n-butyllithium is added dropwise to the reaction at a temperature of −78° C. to room temperature to produce the corresponding lithiated heterocycle. The reaction is then stirred for about 15 minutes and the protected steroid (6) prepared in step A above is added to the reaction. Alternatively, the solution of the lithiated heterocycle can be added to a solution of the protected steroid (6) at a temperature of −78° C. to room temperature. The reaction is stirred for about 4 hours and then the product is isolated and purified by techniques well known in the art, such as extractive methods and flash chromatography. For example, the reaction is diluted with a suitable organic solvent, such as diethyl ether, washed with dilute hydrochloric acid, saturated sodium bicarbonate, brine, dried over anhydrous magnesium sulfate, filtered and concentrated under vacuum. The residue is purified by flash chromatography using a suitable eluent, such as ethyl acetate/hexane on a suitable stationary phase, such as silica gel to provide the $C_{17}$ heterocyclic steroid (7).

In Scheme III, step C the $C_{17}$ heterocyclic steroid (7) is subjected to a dehydration/deprotection reaction to provide the dehydrated/deprotected $C_{17}$ steroid described by formula IIa.

For example, the $C_{17}$ heterocyclic steroid (7) is dissolved in an excess of 4N hydrogen chloride in 1,4-dioxane solution under an atmosphere of nitrogen. The reaction is stirred for 30 minutes to 4 hours and the product is isolated and purified by techniques well known in the art, such as extractive methods and flash chromatography or recrystallization. For example, the reaction is diluted with a suitable organic solvent, such as methylene chloride, washed with saturated sodium bicarbonate, brine, dried over anhydrous magnesium sulfate, filtered and concentrated under vacuum. The residue can be purified by recrystallization from a suitable solvent, such as aqueous methanol or aqueous acetone to provide the dehydrated/deprotected $C_{17}$ heterocyclic steroid of formula IIa. Alternatively the residue can be purified by flash chromatography using a suitable eluent, such as ethyl acetate/hexane on a suitable stationary phase, such as silica gel to provide the dehydrated/deprotected $C_{17}$ heterocyclic steroid of formula IIa.

In Scheme III, step D the 3-hydroxy substituent on the dehydrated/deprotected $C_{17}$ heterocyclic steroid of formula IIa is oxidized to the 3-ketone derivative of the $C_{17}$ heterocyclic steroid described by formula IIb in an analogous manner to the procedure previously described in Scheme I, step C.

It is understood that the configurations encompassed by the stereoisomers of formulas (I) and (II) are readily prepared by one skilled in the art.

The following examples present typical syntheses as described by Schemes I, II and III. These examples are understood to be illustrative only and are not intended to limit the scope of the invention in any way. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor and "δ" refers to parts per million downfield from tetramethylsilane.

EXAMPLE 1A

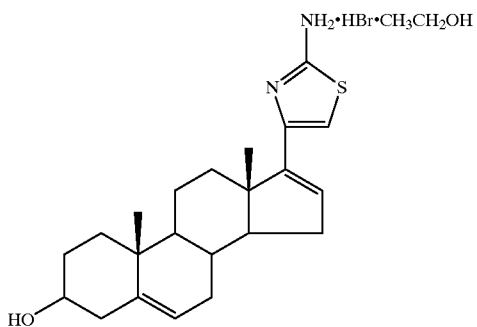

Preparation of (3β)-17-(2-amino-4-thiazolyll-androsta-5,16-dien-3-ol HBr.CH₃CH₂OH Scheme I, step A; Dissolve pregnenolone (1.58 g, 5.00 mmol) in methanol (180 mL) and treat with copper(II) bromide (6.7 g, 30.0 mmol). Heat the reaction at reflux for 24 hours. After cooling, filter the reaction and concentrate the filtrate under vacuum. Dissolve the residue in methylene chloride (75 mL) and wash with water (125 mL). Extract the aqueous wash with methylene chloride (25 mL), combine the organic phases and rinse with half-saturated sodium bicarbonate (2×100 mL) followed by a brine (50 mL). Dry the organic phase over anhydrous sodium sulfate, filter and concentrate under vacuum to provide a yellow oily foam (2.3 g). This is purified by recrystallization from acetone to provide 21-bromo-3β-hydroxy -17α-methoxy-5-pregnen-20-one (428 mg) as a white crystalline solid (See Numazawa, M. and Nagaoka, M., *J. Org. Chem.* (1985), 50, 81 for the literature preparation of this compound).

Scheme I, step B; The 21-bromo-3β-hydroxy-17α-methoxy-5-pregnen-20-one (638 mg, 1.50 mmol) is suspended in ethanol (25 mL) and thiourea (126 mg, 1.65 mmol) is added. The reaction is heated at reflux for 1.5 hours allowing half of the solvent to distill off. Allow the reaction to cool to room temperature and filter. Wasn the precipitate with ethanol (2×1 mL). Dry the resulting white solid under high vacuum to provide the title compound (369 mg), mp 255–260° C. (dec.).

Anal. Calcd for $C_{22}E_{30}N_2OS.HBr.CH_3CH_2OH$: C, 57.94; H, 7.49; N, 5.63; S, 6.44.

Found: C, 57.54; H, 7.31; N, 5.66; S, 6.84. C, 57.61; H, 7.35; N, 5.65.

EXAMPLE 1B

Preparation of (3β)-17-(2-amino-4-thiazolyl)-androsta-5,16-dien-3-ol.HBr.CH₃CH₂OH Scheme II, step A; Dissolve 16-dehydropregnenolone (5.00 g, 15.90 mmol) and 5,5-dibromobarbituric acid (4.55 g, 15.90 mmol) in tetrahydrofuran (60 mL). Add concentrated aqueous hydrogen bromide (100 μL of a 48% solution) to the stirring solution and heat the reaction at reflux for 1 hour. Cool slightly and then concentrate under vacuum to produce a brown oily foam. Dissolve the residue in methylene chloride (350 mL), rinse with 50% saturated sodium bicarbonate (2×200 mL, brine (125 mL), dry over anhydrous magnesium sulfate, filter and concentrate under vacuum to provide 21-bromo-3β-hydroxypregna-5,16-dien-20-one (6.53 g) as an orange-brown solid, slightly contaminated with starting material.

Scheme II, step B; Suspend 21-bromo-3β-hydroxypregna-5,16-dien-20-one (16 mmol) in ethanol (260 mL) and add thiourea (1.33 g, 17.5 mmol). Heat the reaction at reflux for 1 hour and distill off approximately half of the solvent. Allow the reaction to cool to room temperature. Collect the solid by filtration and dry under high vacuum to provide the title compound (3.62 g) as a bright yellow solid. Concentrate the filtrate to approximately 20 mL to provide a second crop, dry under high vacuum and combine with the first crop to provide a total of 4.25 g. Recrystallize this from ethanol to provide the title compound (2.77 g) as a white crystalline solid, mp 258–260° C. (dec); $^1$H NMR (DMSO-$d_6$) δ8.85 (broad singlet, 2H), 6.81 (s, 1H), 6.28 (dd, 1H, J=1.9, 3.3 Hz), 5.29 (broad doublet, 1H, J=4.7 hz), 3.43 (q, 2H, J=7.0 Hz), 3.32–3.18 (m, 1H), 1.05 (t, 3H, J=7.0 Hz), 0.99 (s, 3H), 0.94 (s, 3H); $^{13}$C NMR (DMSO-$d_6$) δ169.4, 142.5, 141.6, 135.6, 131.0, 120.1, 102.0, 69.9, 56.4, 55.9, 49.7, 46.1, 42.2, 36.8, 36.2, 34.4, 31.3, 31.2, 30.8, 29.7, 20.4, 19.0, 18.5, 15.8; MS (CI,CH$_4$) m/z (rel. intensity) 371 (MR$^+$, 76), 370 (33), 369 (34), 353 (100), 83 (26), 81 (27).

Example 2

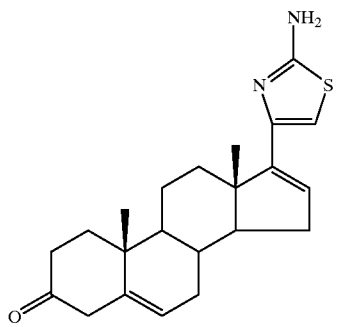

preparation of 17-(2-amino-4-thiazolyl)-androsta-5,16-dien-3one

Scheme I, step C; Dissolve oxalyl chloride (8.86 mL of a 2.0M solution in methylene chloride, 17.73 mmol) in methylene chloride (65 mL) under an atmosphere of nitrogen and cool the solution to −55° C. Add dimethylsulfoxide (1.47 mL, 20.68 mmol) dropwise and stir for 3 minutes. Then add a solution of (3β)-17-(2-amino-4-thiazolyl)-androsta-5,16-dien-3-ol.HBr.CH$_3$CH$_2$OH (2.94 g, 5.91 mmol) prepared in either example 1a or 1b, dissolved in methylene chloride (20 mL) and dimethylsulfoxide (10 mL) to the reaction slowly over 4 minutes and stir for 30 minutes. Then add triethylamine (5.77 mL, 41.36 mmol) and after 5 minutes of stirring allow the reaction to warm to room temperature. Dilute the reaction with methylene chloride (180 mL) and wash with dilute sodium bicarbonate (4×225 mL) and brine/saturated sodium bicarbonate, 3:1 (200 mL). Dry the organic phase over anhydrous magnesium sulfate, filter and concentrate under vacuum to provide a brown foam. Purify by flash chromatography (ethyl acetate/hexane, silica gel) followed crystallization from ethyl acetate/hexane to provide the title compound (135 mg) as a light orange solid after drying under high vacuum at 56° C. for 2 hours, ($R_f$=0.38, 50% ethyl acetate/hexane, SiO$_2$); $^1$H NMR (DMSO-$d_6$) δ6.85 (broad singlet, 2H), 6.45 (s, 1H), 6.06 (broad triplet, 1H, J=1.9, 3.0 Hz), 5.35–5.31 (m, 1H), 3.43 (dq, 1H, J=2.6, 15.9 Hz), 2.67 (dd, 1H, J=1.8, 16.0 Hz), 1.21 (s, 3H), 0.97 (s, 3H); MS (CI/CH$_4$) m/z (rel. intensity) 369 (MH$^+$, 100), 368 (23); HRMS C$_{22}$H$_{29}$N$_2$OS (MH$^+$) calcd 369.2001, observed 369.1989.

EXAMPLE 3

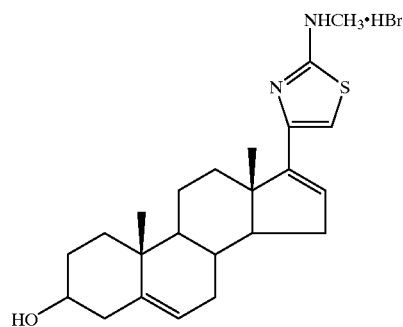

Preparation of (3β)-17-[2-(methylamino)-4-thiazolyl]-androsta-5,16-dien-3-ol.HBr Scheme I, step B; Suspend 21-bromo-3β-hydroxy-17α-methoxy-5-pregnen-20-one (250 mg, 0.59 mmol) prepared in example 1a, step A, in absolute ethanol (15 mL), add 1-methyl-2-thiourea (64 mg, 0.71 mmol) and reflux for 75 minutes allowing the solvent to concentrate to approximately 7 mL. Reflux for an additional hour. Allow the reaction to cool to room temperature, filter and rinse the precipitate with ethanol (2×1 mL). Collect the white solid and dry under high vacuum to provide the title compound (152 mg) as the HBr salt, mp 256–259° C. (dec); $^1$H NMR (DMSO-$d_6$) δ6.86 (broad singlet, 1H), 6.38 (s, 1H), 6.38 (dd, 1H, J=1.9, 3.1 Hz), 5.30 (broad doublet, 1H, J=4.9 Hz), 3.33–3.20 (m, 1H), 3.02 (s, 3H), 1.00 (s, 3H), 0.95 (s, 3H); $^{13}$C NMR (DMSO-$d_6$) δ169.3, 142.7, 141.6, 135.6, 131.5, 120.1, 101.7, 69.9, 56.5, 49.8, 46.3, 42.2, 36.8, 36.2, 34.4, 32.5, 31.4, 31.2, 30.9, 29.8, 20.5, 19.0, 15.9; MS (CI/CH$_4$) m/z (rel. intensity) 385 (MH$^+$, 80), 367 (100), 83 (58), 81 (60); HRMS C$_{23}$H$_{33}$N$_2$O$_6$ (MH$^+$) calcd 385.2314, observed 385.2296.

EXAMPLE 4

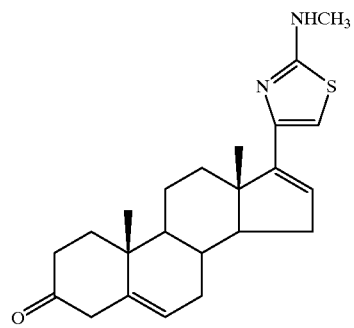

Preparation of 17-[2-(methylamino)-4-thiazolyl]-androsta-5,16-dien-3-one

Scheme I, step C; In an analogous manner to example 2 the title compound is prepared from (3β)-17-[2-(methylamino)-4-thiazolyl]-androsta-5,16-dien-3-ol.HBr prepared in example 3.

EXAMPLE 5

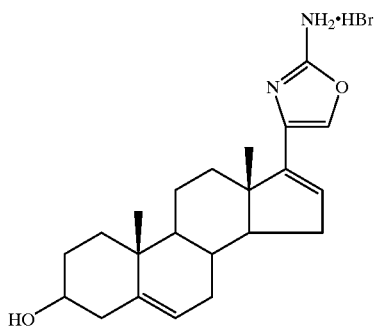

Preparation of (3β)-17-(2-amino-4-oxazolyl)-androsta-5,16-dien-3-ol.HBr

Scheme I, step B; The 21-bromo-3β-hydroxy-17α-methoxy-5-pregnen-20-one (1.50 mmol) prepared in example 1a is suspended in ethanol (25 mL) and urea (1.65 mmol) is added. The reaction is heated at reflux for 1.5 hours allowing half of the solvent to distill off. Allow the reaction to cool to room temperature and filter. Wash the precipitate with ethanol and dry the solid under high vacuum to provide the title compound.

EXAMPLE 6

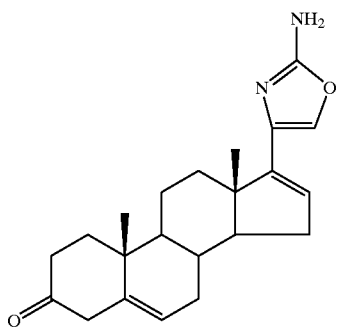

Preparation of 17-(2-amino-4-oxazolyl)-androsta-5,16-dien-3-one

Scheme I, step C; In an analogous manner to example 2 the title compound is prepared from (3β)-17-(2-amino-4-oxazolyl)-androsta-5,16-dien-3-ol.HBr prepared in example 5.

EXAMPLE 7

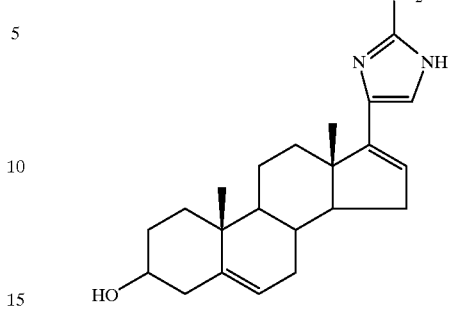

Preparation of (3β)-17-(2-amino-4-imidazolyl)-androsta-5,16-dien-3-ol.HBr

Scheme I, step B; The 21-bromo-3β-hydroxy-17α-methoxy-5-pregnen-20-one (1.50 mmol) prepared in example 1a is suspended in ethanol (25 mL) and guanidine (1.65 mmol) is added. The reaction is heated at reflux for 1.5 hours allowing half of the solvent to distill off. Allow the reaction to cool to room temperature and filter. Wash the precipitate with ethanol and dry the solid under high vacuum to provide the title compound.

EXAMPLE 8

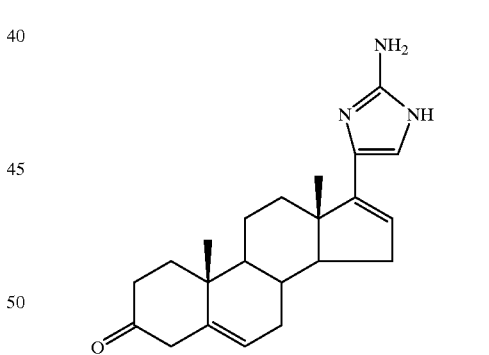

Preparation of 17-(2-amino-4-imidazolyl)-androsta-5,16-dien-3-one

Scheme I, step C; In an analogous manner to example 2 the title compound is prepared from (3β)-17-(2-amino-4-imidazolyl)-androsta-5,16-dien-3-ol.EBr prepared in Example 7.

EXAMPLE 9

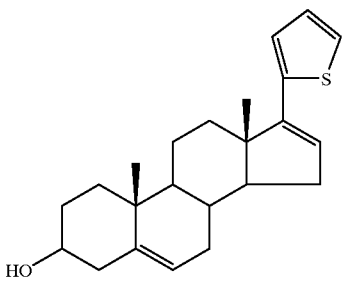

Preparation of (3β)-17-(2-thienyl)-androsta-5,16-dien-3-ol

Scheme III, step A; Dissolve dehydroisoandrosterone (10.0 g, 34.67 mmol) in dimethylformamide (DMF, 150 mL) under an atmosphere of nitrogen. Add t-butyldimethylsilyl chloride (5.23 g, 34.67 mmol), triethylamine (5.32 mL, 38.14 mmol) and a catalytic amount of 4-dimethylaminopyridine (0.21 g, 1.73 mmol) with stirring at room temperature. After two days pour the reaction into rapidly stirring water (1.5 L). Filter the white solid and wash with water (2×50 mL). Dissolve the solid in ethyl acetate (350 ML) and wash with 0.5N hydrochloric acid (2×150 mL), half-saturated sodium bicarbonate (2×150 mL) and brine (100 mL). Dry the organic layer over anhydrous magnesium sulfate, filter and concentrate under vacuum. Purify the residue by flash chromatography (ethyl acetate/hexane, 15:85, silica gel) to provide (3β)-3-[[(1,1-dimethylethyl)dimethylsilyl]oxy]-androst-5-en-17-one (12.60 g) as a white solid, $R_f$=0.78 (ethyl acetate/hexane, 1:1, silica gel), mp 146–148° C.

Scheme III, step B; Dissolve thiophene (0.66 mL, 8.25 mmol) in anhydrous tetrahydrofuran (15 mL) under an atmosphere of nitrogen. Slowly add n-butyllithium (4.69 mL of a 1.6M solution in hexane, 7.5 mmol) to the stirring solution (exothermic reaction). Stir for 15 minutes at room temperature and add (3β)-3-[[(1,1-dimethylethyl)dimethylsilyl]oxy]-androst-5-en-17-one (604 mg, 1.50 mmol) prepared in step A above. Stir the reaction for 4 hours and then dilute with diethyl ether (100 mL). Wash with 0.5N hydrochloric acid (45 mL), saturated sodium bicarbonate (45 mL), brine (30 mL), dry over anhydrous magnesium sulfate, filter and concentrate under vacuum. Purify the residue by flash chromatography (ethyl acetate/hexane, 10:90, silica gel) followed by recrystallization from aqueous acetone to provide (3β,17β)-3-[[(1,1-dimethylethyl)dimethylsilyl]oxy]-17-(2-thienyl) -androst-5-en-17-ol as a blue solid, $R_f$=0.27 (ethyl acetate/hexane, 1:9, silica gel), mp 164–168° C.

Scheme III, step C; Combine (3β,17β)-3-[[(1,1-dimethylethyl)dimethylsilyl]oxy]-17-(2-thienyl)-androst-5-en-17-ol (0.22 g, 0.45 mmol) prepared as in Scheme III, step B above, with 4N hydrogen chloride in 1,4-dioxane (4 mL) under an atmosphere of nitrogen. Stir the reaction for 25 minutes at room temperature. Then pour the reaction into methylene chloride/saturated sodium bicarbonate (50 mL:30 mL) and separate the layers. Wash the organic layer with saturated sodium bicarbonate (2×30 mL), brine (25 mL), dry over anhydrous magnesium sulfate, filter and concentrate under vacuum. Purify the residue by flash chromatography (ethyl acetate/hexane, 30:70, silica gel) to provide the title compound (0.11 g) as a white solid, $R_f$=0.39 (ethyl acetate/hexane, 35:65, silica gel), mp 190–195° C. (dec); $^1$H NMR (CDCl$_3$) δ7.14 (dd,1H, J=1.0, 5.1 Hz), 7.03 (broad doublet, 1H, J=3.5 Hz), 6.97 (dd, 1H, J=3.6, 5.1 Hz), 5.98 (dd, 1H, J=2.0, 3.2 Hz), 5.41–5.37 (m, 1H), 3.60–3.47 (m, 1H), 1.07 (s, 3H), 1.03 (s, 3H); MS (CI/CH$_4$) m/z (rel. intensity) 355 (MH$^+$, 75), 337 (100).

EXAMPLE 10

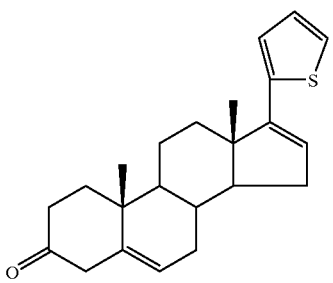

Preparation of 17-(2-thienyl)-androsta-5,16-dien-3-one

Scheme III, step D; In an analogous manner to example 2 the title compound is-prepared from (3β)-17-(2-thienyl)-androsta-5,16-dien-3-ol prepared in example 9.

EXAMPLE 11

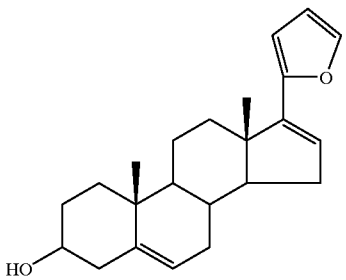

Preparation of (3β)-17-(2-furanyl)-androsta-5,16-dien-3-ol

Scheme III, step B; Dissolve furan (0.60 mL, 8.25 mmol) in anhydrous tetrahydrofuran (15 mL) under an atmosphere of nitrogen and cool to approximately 0° C. Slowly add n-butyllithium (4.69 mL of a 1.6M solution in hexane, 7.5 mmol) to the solution. After 5 minutes, warm the solution to room temperature. After 15 minutes at room temperature add (3β)-3-[[(1,1-dimethylethyl)dimethylsilyl]oxy]-androst-5-en-17-one (604 mg, 1.50 mmol, dissolved in 6 mL of tetrahydrofuran) prepared in example 9, step A, to the reaction with stirring. After 2 hours dilute the reaction with diethyl ether (100 mL) and wash with 0.5N hydrochloric acid (45 mL,, saturated sodium bicarbonate (2×45 mL), brine (45 mL), dry over anhydrous magnesium sulfate, filter and concentrate under vacuum. Purify the residue by flash chromatography (ethyl acetate/hexane, 1:9, silica gel), then recrystallize from aqueous methanol and dry under high vacuum over refluxing ethanol for 3 hours to provide (3β,17β)-3-[[(1,1-dimethylethyl)dimethylsilyl]oxy]-17-(2-furanyl)-androst-5-en-17-ol (302 mg), $R_f$=0.25 (ethyl acetate/hexane, 1:9, silica gel), mp 129–133° C.

Scheme III, step C; Combine (3β,17β)-3-[[(1,1-dimethylethyl)dimethylsilyl]oxyl-17-(2-furanyl)-androst-5- en-17-ol (3 mmol) prepared as in Scheme III, step B above, with 4N hydrogen chloride in 1,4-dioxane (15 mL) under an atmosphere of nitrogen. Stir the reaction for 20 minutes at room temperature. Then pour the reaction into methylene chloride/saturated sodium bicarbonate (200 mL:100 mL) and separate the layers. Wash the organic layer with saturated sodium bicarbonate (100 mL), brine (100 mL), dry over anhydrous magnesium sulfate, filter and concentrate under vacuum. Purify the residue by flash chromatography (ethyl acetate/hexane, 25:75, silica gel) to provide the title compound (0.75 g) as a white solid, $R_f$=0.24 (ethyl acetate/hexane, 3:7, silica gel), mp 105–116° C; $^1$H NMR (CDCl$_3$) δ7.35 (d,1H, J=1.8 Hz), 6.36 (dd, 1H, J=1.8, 3.3 Hz), 6.27 (d, 1H, J=3.3 Hz), 6.07 (dd, 1H, J=2.1, 3.3 Hz), 5.41–5.36 (m, 1H), 3.61–3.48 (m, 1H), 1.07 (s, 3H), 0.99 (s, 3H); MS (CI/CH$_4$) m/z (rel. intensity) 339 (MH$^+$, 55), 338 (42), 337 (36), 321 (100); HRMS C$_{23}$H$_{31}$O$_2$ (MH$^+$) calcd 339.2324, observed 339.2328.

EXAMPLE 12

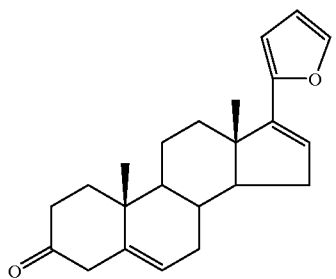

Preparation of 17-(2-furanyl)-androsta-5,16-dien-3-one

Scheme III, step D; In an analogous manner to example 2 the title compound is prepared from (3β)-17-(2-furanyl)-androsta-5,16-dien-3-ol prepared in example 11.

EXAMPLE 13

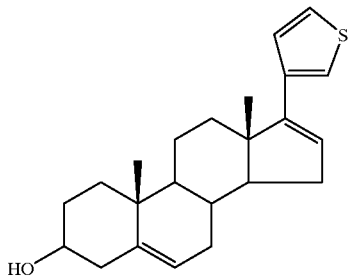

Preparation of (3β)-17-(3-thienyl)-androsta-5,16-dien-3-ol

Scheme III, step B; Dissolve n-butyllithium (7.81 mL of a 1.6M solution in hexane, 12.5 mmol) in tetrahydrofuran (20 mL) under an atmosphere of nitrogen and cool to −78° C. Add dropwise to the solution 3-bromothiophene (1.17 mL, 12.5 mmol). Stir the reaction for 30 minutes and then add a pre-cooled (−78° C.) solution of (3β)-3-[[(1,1-dimethylethyl)dimethylsilyl]oxy]-androst-5-en-17-one (1.01 g, 2.50 mmol) prepared in example 9, step A, in tetrahydrofuran (20 mL). After 1.5 hours pour the reaction into diethyl ether/0.5N hydrochloric acid (150 mL:65 mL) and separate the layers. Wash the organic layer with 0.5N hydrochloric acid (50 mL), saturated sodium bicarbonate (20 mL), brine (25 mL), dry over anhydrous magnesium sulfate, filter and concentrate under vacuum. Purify the residue by flash chromatography (ethyl acetate/hexane, 1:9, silica gel) to provide (3β17β)-3-[[(1,1-dimethylethyl)dimethylsilyl]oxy]17-(3-thienyl)-androst-5-en-17-ol (0.88 g) as a white solid, $R_f$=0.25 (ethyl acetate/hexane, 1:9, silica gel), mp 176–178° C.

Scheme III, step C; Combine (3β,17β)-3-[[(1,1-dimethylethyl)dimethylsilyl]oxy]-17-(3-thienyl)-androst-5-en-17-ol (0.25 g, 0.51 mmol) prepared as in Scheme III, step B above, with 4N hydrogen chloride in 1,4-dioxane (5 mL) under an atmosphere of nitrogen. Stir the reaction for 40 minutes at room temperature. Then dilute the reaction with methylene chloride (35 mL). Wash with saturated sodium bicarbonate (50 mL), brine (30 mL), dry over anhydrous magnesium sulfate, filter and concentrate under vacuum. Purify the residue by recrystallization from acetone to provide the title compound (0.123 g) as a white solid, $R_f$=0.35 (ethyl acetate/hexane, 35:65, silica gel), mp 215–219° C.; $^1$H NMR (CDCl$_3$) δ7.26–7.23 (m, 1H), 7.19 (s, 1H), 7.19–7.17 (m, 1H), 5.93 (dd, 1H, J=1.9, 3.2 Hz), 5.42–5.36 (m, 1s), 3.61–3.43 (m, 1H), 1.07 (s, 3H), 1.03 (s, 3H); MS (CI/CH$_4$) m/z (rel. intensity) 355 (MH$^+$, 77), 354 (35), 353 (25), 337 (100)

EXAMPLE 14

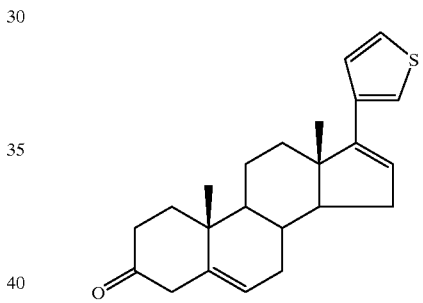

Preparation of 17-(3-thienyl)-androsta-5,16-dien-3-one

Scheme III, step D; In an analogous manner to example 2 the title compound is prepared from (3β)-17-(3-thienyl)-androsta-5,16-dien-3-ol prepared in example 13.

EXAMPLE 15

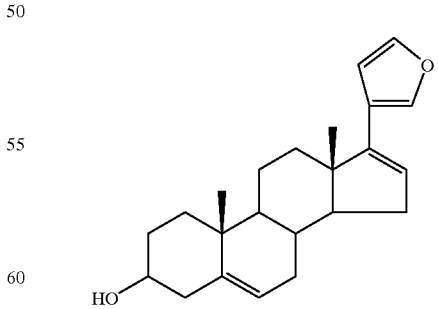

Preparation of (3β)-17-(3-furanyl)-androsta-5,16-dien-3-ol

Scheme III, step B; Dissolve n-butyllithium (15.63 mL of a 1.6M solution in hexane, 25.00 mmol) in anhydrous tetrahydrofuran (30 mL) under an atmosphere of nitrogen and cool to -78° C. Add dropwise to the solution 3-bromofuran (2.25 mL, 25.00 mmol). Stir the reaction for 30 minutes and add a cooled solution (-78° C.) of (3β)-3-[[(1,1-dimethylethyl)dimethylsilyloxy]oxy]-androst-5-en-17-one (2.01 g, 5.00 mmol) prepared in example 9, step A, in tetrahydrofuran (40 mL) to the reaction. Stir for 1.5 hours and pour into diethyl ether/0.5N hydrochloric acid (300 mL:125 mL). Separate the layers and wash the organic layer with 0.5N hydrochloric acid (125 ,mL), saturated sodium bicarbonate (3×75 mL), brine (75 mL), dry over anhydrous magnesium sulfate, filter and concentrate under vacuum. Purify the residue by flash chromatography (ethyl acetate/hexane, 10:90, silica gel) to provide the 2.03 g of product as a white solid. Recrystallize 0.2 g of product from aqueous acetone to provide (3β,17β)-3-[[(1,1-dimethylethyl)dimethylsilyl]oxy]-17-(3-furanyl)-androst-5-en-17-ol (0.12 g) as a white solid, $R_f$=0.19 (ethyl acetate/hexane, 1:9, silica gel), mp 156–158° C.

Scheme III, step C; Combine (3β,17βb)-3-[[(1,1-dimethylethyl)dimethylsilyl]oxy]-17-(3-furanyl)-androst-5-en-17-ol (2.50 g, 5.31 mmol) prepared as in Scheme III, step B above, with 4N hydrogen chloride in 1,4-dioxane (35 mL) under an atmosphere of nitrogen. Stir the reaction for 40 minutes at room temperature and then dilute the reaction with methylene chloride (150 mL). Wash the organic layer with water (35 mL), saturated sodium bicarbonate (2×50 mL), brine (30 mL), dry over anhydrous magnesium sulfate, filter and concentrate under vacuum. Purify the residue by flash chromatography (ethyl acetate/hexane, 3:7, silica gel) to provide 1.05 g of product as a white solid. Recrystallize a portion of the product from aqueous acetone and dry under high vacuum over refluxing ethanol for 4 hours to provide the title compound as a white crystallize solid, $R_f$=0.43 (ethyl acetate/hexane, 35:65, silica gel), mp 186–189° C.; $^1$H NMR (CDCl$_3$) δ7.47 (broad singlet, 1H), 7.36 (t, 1H, J=1.7 Hz), 6.48 (dd, 1H, J=0.8, 1.8 Hz), 5.83 (dd, 1H, J=1.9, 3.2 Hz), 5.41–5.37 (m, 1H), 3.60–3.48 (m, 1H), 1.07 (s, 3H), 0.96 (s, 3H); MS (CI/CH$_4$) m/z (rel. intensity) 339 (MH$^+$, 68), 338 (55), 337 (28), 321 (100); HRMS C$_{23}$H$_{31}$O$_2$ (MH$^+$) calcd 339.2324, observed 339.2304.

EXAMPLE 16

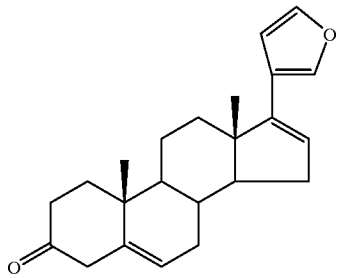

Preparation of 17-(3-furanyl)-androsta-5,16-dien-3-one

Scheme III, step D; In an analogous manner to example 2 the title compound is prepared from (3β)-17-(3-furanyl)-androsta-5,16-dien-3-ol prepared in example 15.

The present invention provides a method of inhibiting the steroid C$_{17-20}$ lyase activity in a patient in need thereof comprising administering to said patient an effective inhibitory amount of a compound of formulas (I) or (II). The present invention further provides a method of treating a patient suffering from an androgen dependent disorder comprising administering to said patient an effective inhibitory amount of a compound of formulas (I) or (II). In addition the present invention provides a method of treating a patient suffering from estrogen dependent disorders comprising administering to said patient an effective inhibitory amount of a compound of formulas (I) or (II).

Patients suffering from androgen dependent disorders, such as prostatic carcinoma, benign prostatic hyperplasia, male pattern baldness, virilism and hirsutism could benefit from a C$_{17-20}$ lyase inhibitor such as a compound of formulas (I) or (II). Patients suffering from estrogen dependent breast cancer could benefit from a C$_{17-20}$ lyase inhibitor such as a compound of formulas (I) or (II).

As used herein, the term "patient" refers to a warm-blooded animal such as a mammal which is suffering from, or is in danger of suffering from an androgen-dependent disorder. It is understood that humans, mice and rats are included within the scope of the term "patient".

Administration of a compound of formulas (I) or (II) to a patient results in inhibition of steroid C$_{17-20}$ lyase activity in the patient. Thus, by treatment of a patient with a compound of formulas (I) or (II), androgen dependent disorders or estrogen dependent disorders are inhibited or suppressed.

A patient is in need of treatment with an agent which inhibits steroid C$_{17-20}$ lyase, such as a compound of formulas (I) or (II), where-the patient is suffering from certain androgen dependent disorders for which elevated activity of steroid C$_{17-20}$ lyase is implicated as a contributing factor in the progression of the disorder.

Based on standard clinical and laboratory tests and procedures, an attending diagnostician, as a person skilled in the art, can readily identify those patients who are in need of treatment with an agent which inhibits steroid C$_{17-20}$ lyase, such as a compound of formulas (I) or (II).

An effective inhibitory amount of a compound of formulas (I) or (II) is that amount which is effective, upon single or multiple dose administration to a patient, in providing an inhibition of steroid C$_{17-20}$ lyase.

An effective inhibitory amount of a compound of formulas (I) or (II) can be readily determined by the attending diagnostician, as one skilled in the art, by the use of known techniques and by observing results obtained under analogous circumstances. In determining the effective amount or dose, a number of factors are considered by the attending diagnostician, including, but not limited to; the species of mammal; its size, age, and general health; the specific androgen-dependent disorder involved; the degree of or involvement or the severity of the disorder; the response of the individual patient; the particular compound administered; the mode of administration; the bioavailability characteristics of the preparation administered; the dose regimen selected; the use of concomitant medication; and other relevant circumstances.

An effective inhibitory amount of a compound of formulas (I) or (II) is expected to vary from about 0.625 milligram per kilogram of body weight per day (mg/kg/day) to about 62.5 mg/kg/day. Preferred amounts are expected to vary from about 5 to about 30 mg/kg/day.

In effecting treatment of a patient, a compound of formulas (I) or (II) can be administered in any form or mode which makes the compound bioavailable in effective amounts, including oral and parenteral routes. For example, compounds of formulas (I) or (II) can be administered orally, subcutaneously, intramuscularly, intravenously, transdermally, intranasally, rectally, and the like. Oral administration and intravenous administration are generally preferred. One skilled in the art of preparing formulations can readily select the proper form and mode of administration depending upon the particular characteristics of the compound selected, the disorder to be treated, the stage of the disorder, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formulas (I) or (II) in admixture or otherwise in association with one or more inert carriers. These compositions are useful, for example, as assay standards, as convenient means of making bulk shipments, or as pharmaceutical compositions. An assayable amount of a compound of formulas (I) or (II) is an amount which is readily measurable by standard assay procedures and techniques as-are well known and appreciated by those skilled in the art. Assayable amounts of a compound of formulas (I) or (II) will generally vary from about 0.001% to about 75% of the composition by weight. Inert carriers can be any material which does not degrade or otherwise covalently react with a compound of formulas (I) or (II). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective inhibitory amount of a compound of formulas (I) or (II) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl. alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formulas (I) and (II) in their end-use application.

Compounds of the formula (I) wherein X is OH are generally preferred. Compounds of the formula (I) wherein Y is S are generally preferred. Compounds of the formula (I) wherein $C_{4-5}$ is a single bond and $C_{5-6}$ is a double bond are generally preferred.

Compounds of the formula (II) wherein X is OH are generally preferred. Compounds of formula (II.) wherein W is 3-furanyl are generally preferred. Compounds of the formula (II) wherein $C_{4-5}$ is a single bond and $C_{5-6}$ is a double bond are generally preferred.

The following list illustrates compounds according to the present invention:
1) 17-(2-amino-4-thiazolyl)androsta-5,16-dien-3β-ol.HBr.CH$_3$CH$_2$OH;

2) 17-(2-amino-4-thiazolyl)androsta-5,16-dien-3β-ol;
3) 17-(2-amino-4-thiazolyl)androsta-5,16-dien-3-one;
4) 17-[2-(methylamino)-4-thiazolyl]androsta-5,16-dien-3β-ol.HBr;
5) 17-[2-(methylamino)-4-thiazolyl]androsta-5,16-dien-3-one;
6) 17-(2-amino-4-oxazolyl)androsta-5,16-dien-3β-ol. HBr;
7) 17-(2-amino-4-oxazolyl)androsta-5,16-dien-3-one;
8) 17-(2-amino-4-imidazolyl)androsta-5,16-dien-3β-ol.HBr;
9) 17-(2-amino-4-imidazolyl)androsta-5,16-dien-3-one;
10) 17-(2-thienyl)androsta-5,16-dien-3β-ol;
11) 17-(2-thienyl)androsta-5,16-dien-3-one;
12) 17-(2-thienyl)androsta-5,16-dien-3-one;
13) 17-(2-furanyl)androsta-5,16-dien-3β-ol;
14) 17-(2-furanyl)androsta-5,16-dien-3-one;
15) 17-(3-thienyl)androsta-5,16-dien-3β-ol;
16) 17-(3-thienyl)androsta-5,16-dien-3-one;
17) 17-(3-furanyl)androsta-5,16-dien-3β-ol;
18) 17-(3-furanyl) androsta-5,16-dien-3-one.

The following studies illustrate the utility of the compounds of formulas (I) and (II). These studies are understood to be illustrative only and are not intended to limit the scope of the invention in any way. As used here in the following terms have the indicated meanings: "mM" refers to millimolar concentration; "μm" refers to micromolar concentration; "Units" refers to the internationally accepted measurement of protein; "S.D." refers to standard deviation; "ηmol" refers to nanomoles; "μg" refers to micrograms; "ηg" refers to nanograms "μL" refers to microliters; "mCi" refers to millicuries; "μCi" refers to microcuries.

In Vitro Activity

Utilizing an invitro assay, the activity of the compounds of formulas (I) and (II) as inhibitors of steroid $C_{17-20}$ lyase are established using microsomal preparations of the enzyme from human or cynomolgus monkey testicular tissue. Human testes were acquired from therapeutic orchiectomies. Microsomes are isolated from human or cynomolgus monkey tissue. The compound to be tested is dissolved in dimethyl sulfoxide and diluted in 0.05M potassium phosphate buffer, pH 7.4, to give the desired concentrations of test compound. Assays contain an NADPH regenerating system comprised of 1 mM NADPH, 5 mM glucose-6-phosphate, 1 IU/mL glucose-6-phosphate dehydrogenase and microsomal protein in a total volume of 0.2 mL. Control assays contain all components, including dimethyl sulfoxide, but no test compound. All assays are performed in duplicate. For determination of time dependent $C_{17-20}$ lyase inactivation, the test compound is incubated with 20 to 62 μg/mL microsomal protein, buffer and the NADPH regenerating system described above at 34° C. for 0 or 40 minutes. Aliquots of 180 μL are then removed and assayed for enzyme activity by addition to 7-$^3$H-17α-hydroxypregnenolone (11.2 mCi/mmole; 0.2 μCi per assay) plus unlabeled 17α-hydroxypregnenolone to give a total substrate concentration of 1.0 μM or 0.3 μM per assay and are subsequently incubated at 34° C. for 6 minutes. For determination of reversible inhibition by the test compound, the reaction is initiated by the addition of substrate, 7-$^3$H-17 α-hydroxypregnenolone (11.2 mCi/mmole; 0.20 μCi per assay) plus unlabeled 17μ-hydroxypregnenolone to yield a final concentration of 0.3 μM (=Km), to the other assay components. The complete assay is incubated at 34° C. for 6 minutes. Each assay is terminated by addition of 5 mL of chloroform/methanol (2:1). Carrier steroids representing substrates and products (17α-hydroxypregnenolone, dehydroepiandrosterone, and androst-5-ene-3β,17β-diol and 0.8 mL of distilled, deionized water are also added at this time. The steroids are extracted by the method of Moore and Wilson (Methods in Enzymol., eds. O'Malley, B. W. and Hardman, J. G. 36, 1975, pp.466–474). The organic phase containing the steroids is evaporated using nitrogen gas, the residue is dissolved in 18% tetrahydrofuran (v/v) in hexane and the steroids are separated by HPLC on an Si60 (5 μm) column (250×4 mm) using a gradient of 18–22% tetrahydrofuran (v/v) in hexane. Radioactivity in the steroid peaks is measured using a Radiometric Model HS or Model A515 Flo-One detector.

The enzyme activity for each assay is calculated from the percent conversion of substrate to products, and the results are expressed as percent inhibition of control.

$IC_{50}$ values are determined by fitting these data to a two parameter dose-response equation. When compounds of formulas (I) and (II) are tested in the above procedure, the following results presented in Tables 1, 2 and 3 are observed.

Table 1

Screen for Time-Dependent Inhibition of Human Testicular $C_{17-20}$ Lyase by 17-(2-amino-4-thiazolyl)androsta-5,16-dien-3β-ol.HBr.CH$_3$CH$_2$OH

| Compound | Preincubation Time (min.) | Conc. (μm) | Inhibition (%) |
|---|---|---|---|
| 17-(2-amino-4-thiazolyl)androsta-5,16-dien-3β-o1.HBr.CH$_3$CH$_2$OH | 0 | 10 | 62 |
| | 0 | 1 | 44 |
| | 40 | 10 | 29 |
| | 40 | 1 | 32 |

Table 2

Screen for Time-Dependent Inhibition of Cynomolgus Monkey

Testicular $C_{17-20}$ Lyase by 17-(2-(methylamino)-4-thiazolyl]androsta-5,16-dien-3β-ol.HBr and Inhibition of Cynomolgus Monkey Testicular $C_{17-20}$ Lyase by 17-(2-amino-4-thiazolyl) androsta-5,16-dien-3-one

| Compound | Preincubation Time (min.) | Conc. (μm) | Inhibition (%) |
|---|---|---|---|
| 17-(2-methylamino)-4-thizaolyl]androsta-5,16-dien-3β-o1.HBr | 0 | 10 | 40 |
| | 0 | 1 | 28 |
| | 40 | 10 | 80 |
| | 40 | 1 | 26 |
| 17-(2-amino-4-thiazolyl)androsta-5,16-dien-3-one | 0 | 10 | 92 |
| | 0 | 1 | 66 |

Table 3

Screen for Inhibition of Cynomolgus Monkey Testicular $C_{17-20}$ Lyase by Various Compounds of Formula (II)

| Compound | Conc. (μM) | Inhibition (%) |
|---|---|---|
| 17-(2-thienyl)androsta-5,16-dien-3β-o1 | 1 | 75 |
| | 0.1 | 43 |
| 17-(2-furanyl)androsta-5,16-dien-3β-o1 | 1 | 72 |
| | 0.1 | 10 |
| 17-(3-thienyl)androsta-5,16-dien-3β-o1 | 1 | 42 |
| | 0.1 | 21 |
| 17-(3-furanyl)androsta-5,16-dien-3β-o1 | 1 | 91 |
| | 0.1 | 53 |

What is claimed is:

1. A method of inhibiting the steroid $C_{17-20}$ lyase activity in a patient in need thereof comprising administering to said patient an effective inhibitory amount of a compound of the formula:

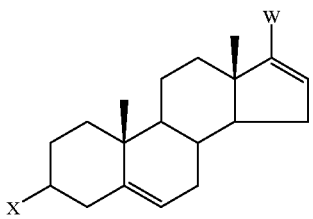

wherein

X is =O or —OH;

W is selected from the group consisting of:

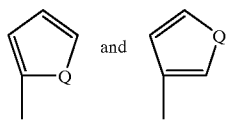

wherein

Q is O.

2. The method according to claim 1 wherein X is OH.

3. The method according to claim 1 wherein X is O.

4. The method according to claim 1 wherein the compound is 17-(2-furanyl) androsta-5,16-dien-3β-ol.

5. The method according to claim 1 wherein the compound is 17-(3-furanyl) androsta-5,16-dien-3β-ol.

6. The method according to claim 1 wherein the compound is 17-(2-furanyl) androsta-5,16-dien-3-one.

7. The method according to claim 1 wherein the compound is 17-(3-furanyl) androsta-5,16-dien-3-one.

8. A method of inhibiting the steroid $C_{17-20}$ lyase activity in a patient in need thereof comprising administering to said patient an effective inhibitory amount of a compound of the formula:

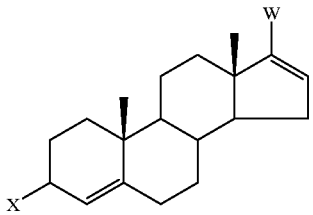

wherein

X is =O or —OH;

W is selected from the group consisting of:

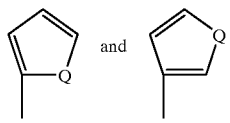

wherein

Q is O.

9. The method according to claim 8 wherein the compound is 17-(2-furanyl) androsta-4,16-dien-3-one.

10. The method according to claim 8 wherein the compound is 17-(3-furanyl) androsta-4,16-dien-3-one.

11. A method of treating a patient suffering from an androgen dependent disorder comprising administering to said patient an effective inhibitory amount of a compound of the formula:

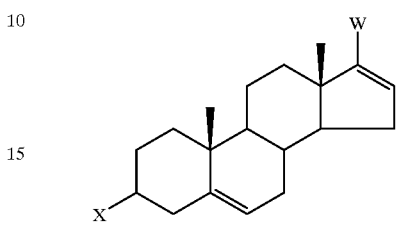

wherein

X is =O or —OH;

W is selected from the group consisting of:

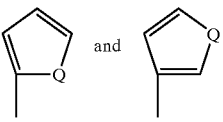

wherein

Q is O.

12. A method of treating a patient suffering from an androgen dependent disorder comprising administering to said patient an effective inhibitory amount of a compound of the formula:

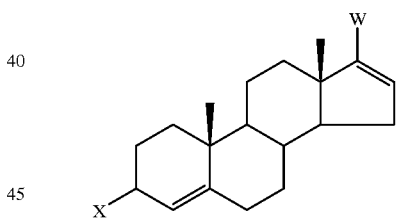

wherein

X is =O or —OH;

W is selected from the group consisting of:

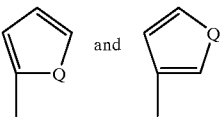

wherein

Q is O.

* * * * *